Figure 1:
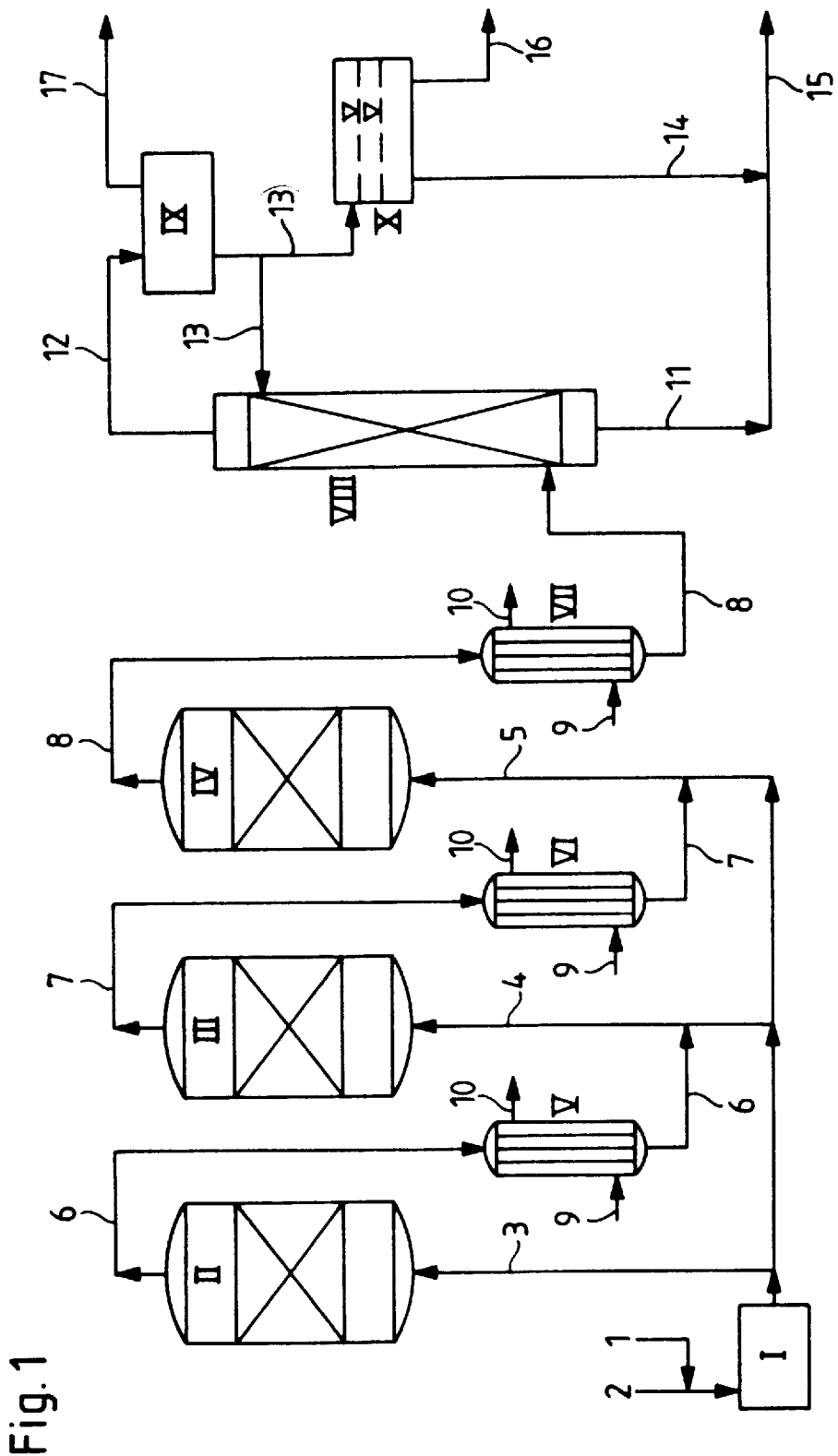

United States Patent [19]
Langer et al.

[11] Patent Number: 5,877,350
[45] Date of Patent: Mar. 2, 1999

[54] PROCESS FOR THE PRODUCTION OF AROMATIC AMINES

[75] Inventors: Reinhard Langer; Hans-Josef Buysch, both of Krefeld; Ursula Pentling, Kempen; Paul Wagner, Düsseldorf, all of Germany

[73] Assignee: Bayer Aktiengesellschaft, Leverkusen, Germany

[21] Appl. No.: 511,164

[22] Filed: Aug. 4, 1995

[30] Foreign Application Priority Data

Aug. 8, 1994 [DE] Germany .................. 44 28 018.1

[51] Int. Cl.$^6$ .................................................. C07C 209/36
[52] U.S. Cl. .................... 564/423; 564/420; 564/421; 564/422
[58] Field of Search .................... 564/420, 421, 564/422, 423

[56] References Cited

U.S. PATENT DOCUMENTS

| | | | |
|---|---|---|---|
| 3,363,152 | 1/1968 | Szigeth .................................. | 260/580 |
| 3,871,445 | 3/1975 | Wanka et al. ........................... | 165/107 |
| 4,265,834 | 5/1981 | Birkenstock et al. .................. | 564/421 |
| 4,732,918 | 3/1988 | Lohmueller et al. ................... | 518/712 |
| 4,740,621 | 4/1988 | Adams et al. ......................... | 564/419 |

FOREIGN PATENT DOCUMENTS

| | | |
|---|---|---|
| 1452466 | 10/1976 | United Kingdom . |
| 2182330 | 5/1987 | United Kingdom . |

OTHER PUBLICATIONS

Hydrocarbon Processing 59 (Nov. 1979) No. 11, p. 136.
Chemical Abstracts, vol. 112, No. 4, Jan. 22, 1990, Abstract No. 2634lt, p. 362; Spalte 2 and CS–A– 258 375 (Pavlas, Pavel et al) Apr. 14, 1989.
Chemical Abstracts, vol. 100, No. 16, Apr. 16, 1984, Abstract No. 123155v, Gramatikov, K. et al "Adiabatic process of catalytic reduction of nitrobenzene to aniline", p. 108, Spalte 2, and IZV. Khim., Bd. 16, Nr. 1–2, 1983 pp. 38–43.
Chemical Abstracts, vol. 117, No. 20, Nov. 16, 1992, Abstract No. 194013j, p. 120; Spalte 2, & CS–A–263 430 (Rozinek, Radovan et al) Jan. 20, 1992.

*Primary Examiner*—Peter O'Sullivan
*Attorney, Agent, or Firm*—Joseph C. Gil; Lyndanne M. Whalen

[57] ABSTRACT

Aromatic amines are produced by hydrogenation of the appropriate aromatic nitro compounds in the vapour phase on fixed catalysts. The catalysts contain supported metals active in hydrogenation, the reaction is carried out under adiabatic conditions at a pressure of from 1 to 30 bar, an inlet temperature of from 200° to 400° C. and a maximum catalyst temperature of 500° C.

31 Claims, 2 Drawing Sheets

PROCESS FOR THE PRODUCTION OF AROMATIC AMINES

The present invention provides a process for the hydrogenation of aromatic nitro compounds to aromatic amine compounds in the vapour phase on fixed catalysts, wherein neither is heat supplied from outside nor is heat withdrawn, that is, the process is carried out adiabatically.

Aromatic amines are important intermediate products which have to be available at a reasonable price and in large quantities. For this reason, for the hydrogenation of nitrobenzene, for example, plants having very large capacities must be built.

The hydrogenation of aromatic nitro compounds is a highly exothermic reaction. Thus about 488 kJ/mol (117 kcal/mol) is liberated in the hydrogenation of nitroxylene to xylidine at 200° C., and about 544 kJ/mol (130 kcal/mol) is liberated in the hydrogenation of nitrobenzene.

The removal and utilisation of the heat of reaction is consequently an important feature in carrying out processes for the hydrogenation of aromatic nitro compounds.

Thus in one established procedure, the catalyst is operated as a fluidised, thermostabilised bed (U.S. Pat. No. 3,136,818). The efficient removal of heat by this process is confronted with problems owing to non-uniform residence-time distribution (leakage of nitrobenzene) and catalyst attrition.

Narrow residence-time distributions and low catalyst attrition may occur in reactors having a stationary catalyst bed. However, in these reactors problems arise in connection with the thermostatic control of the catalyst beds. In general thermostatically-controlled multitubular reactors are used which, especially in the case of large reactors, have a very complicated cooling cycle (DE-OS 22 01 528, DE-OS 34 14 714).

Reactors of this kind are complex and involve high investment costs. Problems relating to mechanical strength and uniform thermostatic control of the catalyst bed, which increase rapidly with the size of the reactor, render large units of this type uneconomic.

Single reactors, which are employed for the process according to the invention described in more detail below, contain only catalyst beds and have no system for heat balance inside the reactor. They are easily transferred to an industrial scale and are economically-priced and robust in all sizes. The reaction enthalpy is reflected quantitatively in this type of reactor in the temperature difference between the educt gas stream and the product gas stream.

Hitherto neither has the use of such reactors been described, nor have suitable catalysts and suitable operating methods been demonstrated for the highly exothermic hydrogenation of aromatic nitro compounds.

GB 1 452 466 relates to a process for the hydrogenation of nitrobenzene wherein an adiabatic reactor is connected to an isothermal reactor. Here the greater part of the nitrobenzene is reacted in a thermostatically-controlled multitubular reactor; only the hydrogenation of the residual content of nitrobenzene is carried out at a relatively low excess of hydrogen (less than 30:1) in an adiabatic reactor.

The advantage of completely dispensing with a thermostatically-controlled reactor in a purely adiabatic reaction was not seen.

DE-AS 18 09 711 relates to the steady introduction of liquid nitro compounds into a hot gas stream by atomisation, preferably at restricted points immediately upstream from the reactor. The design of the reactor is not considered in the application document. It can however be inferred from the Example that, in spite of a considerable excess of hydrogen, at least 34% of the reaction enthalpy has not left the reactor with the product gas.

In DE-OS 36 36 984, there is described a process for the combined production of aromatic nitro and aromatic dinitro compounds from the corresponding hydrocarbons by nitration and subsequent hydrogenation. The hydrogenation is carried out in the vapour phase at temperatures of between 176° and 343.5° C. The emphasis of this DE-OS is on utilising the lowering of the melting points of mono-/dinitrobenzene mixtures and of amino/diaminobenzene mixtures. By this means the products of both the nitration and the hydrogenation can also be handled in solid form, therefore without solvent, with no crystallisation problems. The idea of carrying out the reaction adiabatically cannot be inferred from this DE-OS.

That new, improved plants for the hydrogenation of nitrobenzene to aniline have been put into operation may be learned from the journal "Hydrocarbon Processing 59" (Vol. 59, 1979, Number 11, page 136). It can be inferred from this publication that the recovery of vapour and the reaction are carried out closely connected in one processing step.

In all the above-mentioned publications Cu catalysts are employed which are operated entirely in small loadings (less than 0.1 g (nitrobenzene)/ml(catalyst).h) and at a low temperature level. This results in low production outputs.

Besides the copper catalysts mentioned, numerous other contacts for the vapour-phase hydrogenation of aromatic nitro compounds are described. They are described in many publications and include as elements and compounds active in hydrogenation Pd. Pt, Ru, Fe, Co, Ni, Mn, Re, Cr, Mo, V, Pb, Ti, Sn, Dy, Zn, Cd, Ba, Cu, Ag, Au, partly as oxides, sulphides or selenides as well as in the form of a Raney alloy, on supports such as $Al_2O_3$, $Fe_2O_3/Al_2O_3$, $Sio_2$, silicates, carbons, $TiO_2$, $Cr_2O_3$.

These catalysts are also operated using small loadings in a temperature range below 350° C.

The invention relates to a process for the production of aromatic amines of the formula

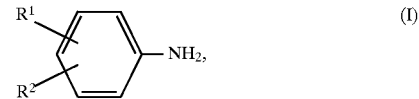

wherein
$R^1$ and $R^2$ independently of one another signify hydrogen, methyl or ethyl, wherein $R^1$ can also signify amino,
by hydrogenation of aromatic nitro compounds of the formula

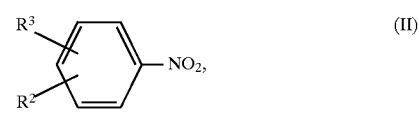

wherein
$R^2$ and $R^3$ independently of one another signify hydrogen, methyl or ethyl, wherein $R^3$ can also signify nitro,
using $H_2$ on fixed catalysts, which is characterised in that the process is carried out under adiabatic conditions at a pressure of from 1 to 30 bar, an inlet temperature of the aromatic nitro compound/$H_2$ mixture of from 200° to 400° C. and at a maximum catalyst temperature of 500° C.

Preferred aromatic nitro compounds for the process according to the invention are those of the formula

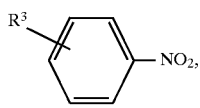

wherein
R³ has the meaning given above.

The aromatic nitro compound is particularly preferably nitrobenzene.

A production plant according to the invention consists of at least one adiabatic reactor supplied with a stationary catalyst. At most 10, preferably at most 5, particularly preferably at most 3 of these reactors are connected in series. Each of the reactors connected in series can be substituted by several reactors connected in parallel. At most 5, preferably at most 3, particularly preferably at most 2 reactors are connected in parallel as a substitute for one reactor. The process according to the invention can accordingly include at most 50 and at least one reactor.

Several reactors having one catalyst bed can be substituted by fewer reactors having several catalyst beds.

The reactors consist of single containers having insulated catalyst beds, which are described, for example, in Ullmanns Encyclopedia of Industrial Chemistry (fifth, completely revised edition, Volume B4, pages 95–102, pages 210–216).

The catalyst beds are installed on or between gas-permeable walls, as in the prior art. Especially in the case of thin beds, technical devices are installed above, underneath or above and underneath the bed for uniform distribution of gas. These devices can be perforated plates, bubble trays, valve trays or other baffles which bring about a uniform entry of the gas into the catalyst bed by producing a small, but steady drop in pressure. It is preferable to use metal or ceramic sintered mats, which are sold, for example, by the firm Krebsöge.

Instead of catalyst beds, suitable packing can be used as the support material. This could be, for example, honeycomb bodies or corrugated layers, which are sold by the firm Sulzer under the trade name Katapak. The said packings are activated for the use according to the invention by the deposition thereon of suitable metal compounds prior to introduction into the reactor.

Upstream from each catalyst bed, fresh aromatic nitro compound is fed into the circulating gas stream, which consists mainly of recycled and freshly added hydrogen. This can take place in the manner described in DE 18 09 711, but the aromatic nitro compound is preferably completely vaporised in the fresh hydrogen and then introduced in vapour form into the circulating gas stream. The advantage of this procedure lies in the markedly lower formation of deposits in the reactor and in the feed pipes. The vaporisation can be carried out as in the prior art in known evaporators, such as, for example, downflow evaporators, ascension pipe evaporators, injection evaporators, film evaporators, circulation evaporators and spiral evaporators. Vaporisation is conducted preferably in downflow evaporators and injection evaporators, particularly preferably in downflow evaporators. It is also possible to atomise the liquid aromatic nitro compounds into the stream of fresh hydrogen or of circulating hydrogen by means of one-fluid or two-fluid nozzles, while combination of the stream of educt gas can take place after superheating in a heat exchanger. A generally known mist eliminator can be connected to the vaporising unit. The educt gas stream is mingled with the circulating stream in a known manner by means of appropriate feed devices and distribution devices or by mixing devices such as, for example, mixers of the type SUX or SMV, obtainable from the firms Sulzer or Kenics.

The product gas leaving each catalyst bed is cooled, with recovery of vapour. For this purpose, the product gas is passed through one or more heat exchangers. These can be the heat exchangers known to the person skilled in the art, for example, shell-and-tube heat exchangers, plate heat exchangers, ringnut heat exchangers, spiral flow heat exchangers or fin-tube heat exchangers.

After leaving the last heat exchanger employed for the production of vapour, the product gas is cooled in order to remove from the reaction mixture aromatic amine and water of reaction. The remaining circulating gas is then returned to the first reactor, after diverting a small quantity of gas in order to maintain constant the gaseous components of the circulating gas, which are partly carried over with the educts, mainly the fresh hydrogen, and are partly formed on the contact ($N_2$, $NH_3$). Prior to being returned to the first reactor, the remaining gas must be heated up to the inlet temperature and contain freshly added educt.

The cooling of the product gas and the heating of the circulating gas is advantageously carried out—after removal of the condensable product and diversion of the discarded circulating gas—by passing the gas streams past one another countercurrently through heat exchangers.

The circulating gas is again brought to the inlet temperature by means of a heat exchanger immediately upstream from the first reactor. Aromatic nitro compound and fresh hydrogen are fed in as described above, beforehand or afterwards, preferably afterwards.

The discharge of the components of the products from the cooled circulating gas stream can be effected by means of partial and/or total condensation or by washing out using cold product or an inert solvent. The gas stream is preferably first of all passed through a scrubber, wherein it encounters the condensate flowing from a cooled condenser connected in series. The scrubber is so operated that the condensate leaving it is one-phase. To this end the condensate leaving the scrubber must be at a specific temperature, depending on the pressure and on the nature of the aromatic amine, so that little or no water is contained in the condensate. The person skilled in the art is familiar with finding the optimal solution to this problem. In the preferred embodiment, there is connected in series to the condenser which operates the scrubber a second condenser, wherein the bulk of the water and a further portion of the aromatic amine are collected. The latter condensate is fed to a device for separating liquid phases (organic and aqueous) . The organic phase together with the condensate from the scrubber is led away to be worked up by distillation. The aqueous phase is also worked up for the purpose of separating off dissolved aromatic amine and delivering the latter to be worked up by distillation.

Depending on the absolute pressure, on leaving the final condenser the circulating gas is at a temperature of between 5° and 95° C., preferably between 10° and 80° C., particularly preferably between 15° and 70° C. and most preferably between 20° and 60° C.

A small quantity of this gas is separated off for removal of the above-mentioned gaseous components.

The circulating gas is then sent to a compressor, passes through the countercurrent heat exchangers and optionally a superheater, in order to be sent to the first reactor. The compressor can in principle be at any point in the gas cycle. Preferably it is positioned at points at which deposits are not to be expected, that is, after the condensation, upstream of the first reactor and at a low temperature.

Figure 2:
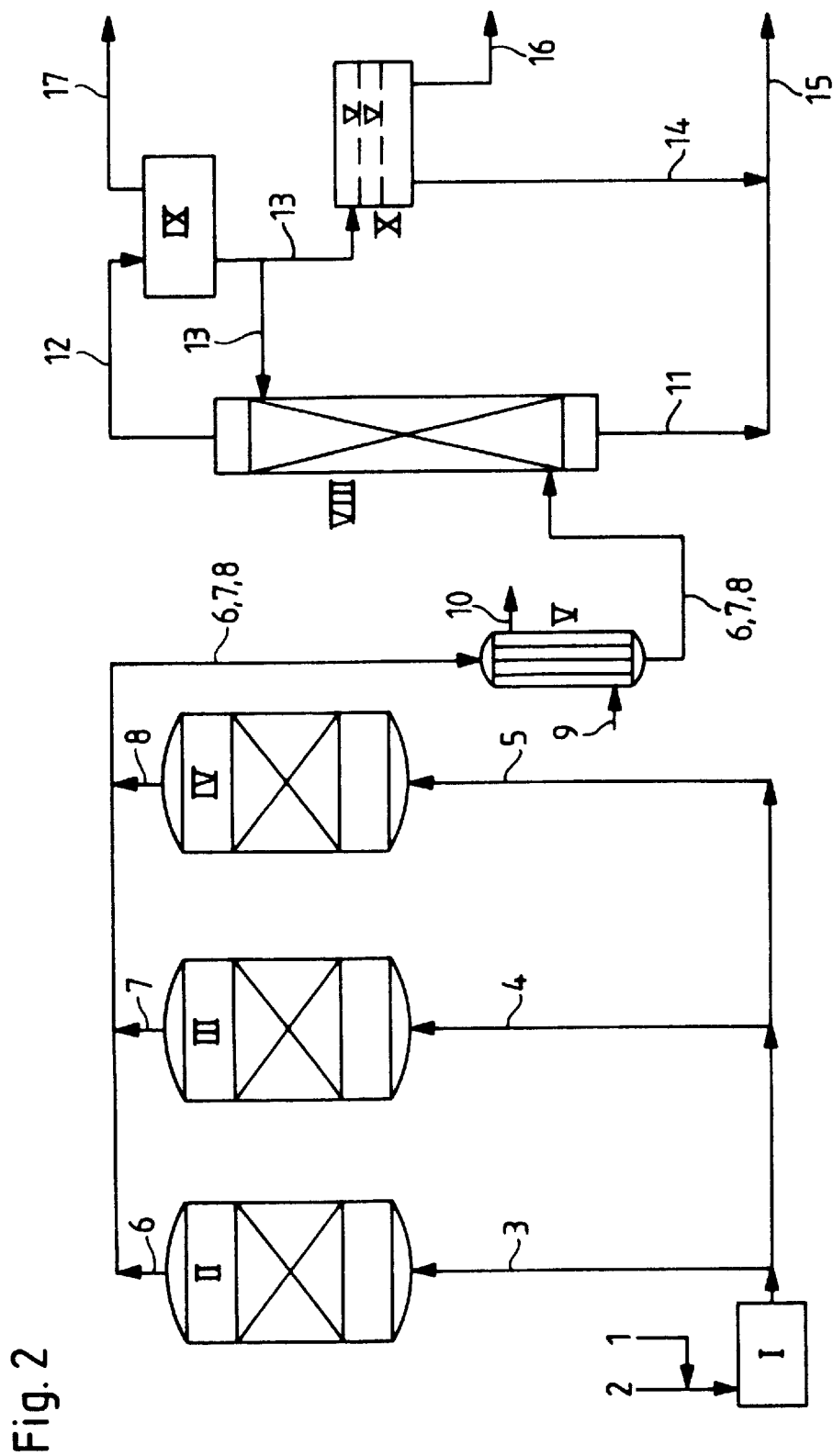

Production plants according to the invention are illustrated by way of example in FIGS. 1 and 2, together with flow rates, pressures and temperatures. The data are not intended to be limiting.

The process according to the invention is operated at pressures of between 1 and 30 bar, preferably of between 1 and 20 bar, particularly preferably of between 1 and 15 bar.

Upstream from each reactor fresh hydrogen and aromatic nitro compound are fed into the circulating gas stream. After homogenisation of the gas mixture formed, between 60 and 800 equivalents, preferably between 80 and 400 equivalents, particularly preferably between 100 and 300 equivalents, and most preferably between 120 and 200 equivalents of hydrogen are present per equivalent of nitro groups.

The temperature of the homogenised mixture of gaseous educts at the inlet to each reactor is between 200° and 400° C., preferably between 230° and 370° C., particularly preferably between 250° and 350° C.

The thickness of the catalyst beds can be between 1 cm and 5 m, preferably between 5 cm and 2 m, particularly preferably between 10 cm and 1 m, most preferably between 30 cm and 60 cm.

All the contacts hitherto described for the vapour phase hydrogenation of nitro compounds can be employed as catalysts. These contain the elements mentioned in more detail above, either as alloys or as mixed oxides and optionally on inert support materials. Particularly suitable support materials are $\alpha$- and $\gamma$-$Al_2O_3$, $SiO_2$, $TiO_2$, terra rossa and limonite, $Fe_2O_3/Al_2O_3$ mixtures, $CuO/Cr_2O_3$ mixtures, waterglass, graphite, activated carbon (BET 20 to 100 $m^2/g$) and carbon fibres. But other supports may in principle also be used.

Preferably catalysts described in DE-OS 28 49 002 are used. These are supported catalysts on inert supports having a BET surface area of less than 20 $m^2/g$, or $\alpha$-$Al_2O_3$ having a BET surface area of less than 10 $m^2/g$. The preparatory treatment described in DE-OS 28 49 002 using a base is not absolutely necessary.

Three classes of active substances are deposited on the support material:

a) 1 to 100 g/l of a catalyst consisting of one or more metals of the Groups VIII$a$, I$b$ and II$b$ of the periodic table of elements (Mendeleev), b) 1 to 100 g/l of one or more transition metals of the groups II$b$, IV$a$, V$a$ and VI$a$ and c) 1 to 100 g/l of one or more of the main group elements of the groups IV$b$ and V$b$.

Elements of the group II$b$ can therefore act as active substances (a) and (b). Preferred active substances are Pd as metal (a), V, Nb, Ta, Cr, Mo, W, Ti as transition metal (b) and Pb and Bi as the main group elements (c).

Particularly preferably (a) from 20 to 60 g of Pd, (b) from 20 to 60 g of V and (c) from 10 to 40 g of Pb are applied to the support.

The active substances are applied to the support in the form of their soluble salts; several treatments (impregnations) per component may be required. In a preferred method the active substances only form shells, that is, they are applied close to the surface of the catalyst.

These contacts are operated at a temperature ranging from the inlet temperature of the educt gas up to a maximum of 500° C., preferably up to a maximum of 480° C., particularly preferably up to a maximum of 460° C. and most preferably, up to a maximum of 440° C.

Other preferred catalysts are those supporting Pd alone or together with Rh and/or Ir and/or Ru on carbon supports having low BET surface areas. These support materials contain graphite as actual graphites and cokes, such as needle coke or petroleum coke. These supports have a BET surface area of from 0.2 to 10 $m^2/g$. According to the invention catalysts are used which contain from 0.001 to 1.5% by weight of Pd, referred to the total weight of the catalyst, with substitution by from 0 to 40% by weight, relative to the weight of the Pd, of Ir and/or Rh and/or Ru being possible, on graphite or graphite-containing coke as a support. These catalysts therefore contain the precious metal (s) in the following arrangements on the support: Pd alone, Pd/Ir, Pd/Rh, Pd/Ru, Pd/Ir/Rh, Pd/Ir/Ru, Pd/Rh/Ru, Pd/Ir/Rh/Ru. In many cases one of the said dual combinations or Pd alone are used. In a preferred method, palladium in a quantity of from 0.005 to 1% by weight, preferably from 0.05 to 0.5% by weight, referred to the total weight of the catalyst, is present in the catalysts on carbon supports. The lower limit of zero for the relative percentages of the other platinum metals mentioned above indicates the use of Pd alone. If the other platinum metals are used, the proportion thereof is preferably from 10 to 40 relative per cent in total; among them the ratio of their weights is from 1:1 to 3:1 for each pair.

It has moreover proved of advantage to dope the said catalysts additionally with sulphur-containing or phosphorus-containing, preferably phosphorus-containing, compounds. This additional content of doping agent is from 0.1 to 2% by weight, preferably from 0.1 to 1% by weight, of sulphur or phosphorus, preferably phosphorus, in chemically bonded form, referred to the total weight of the catalyst. Examples of preferred phosphorus-containing compounds for doping the catalysts according to the invention are: the oxy acids of phosphoric acid $H_3PO_4$, $H_3PO_3$, $H_3PO_2$ or the alkaline salts thereof, for example, sodium dihydrogen phosphate, sodium phosphate or potassium phosphate or sodium hypophosphite.

A possible process for producing the catalysts on carbon supports is to apply the above-mentioned precious metals in the form of suitable salts and also the sulphur-containing or phosphorus-containing compound in separate operations to one of the above-mentioned supports in the form of pellets, spheres, granules or broken pieces of about 1 to 10 mm in size, with drying after each application. Drying is carried out in a known manner, preferably at between 100 and 140° C. and at reduced to normal pressure, for example, from 1 to 1,000 mbar; the reduced pressure is suitably provided, for example, by a water suction pump. Aqueous solutions can be employed to impregnate the support; this is preferably the case with the sulphur-containing or phosphorus-containing compounds, of which water-soluble examples are preferred. The salts of precious metals, however, are preferably dissolved and applied in organic solvents such as simple alcohols, ketones, cyclic ethers or nitriles. Examples of such organic solvents are methanol, ethanol, propanol, isopropanol, acetone, methyl ethyl ketone, dioxane, acetonitrile and comparable solvents. Methylene chloride and comparable solvents can also be used in the case of salts containing organic anions. Suitable salts of the precious metals are, for example, chlorides, nitrates or acetates thereof.

After impregnation and subsequent drying, the catalyst is available for use. It is activated preferably in the reactor by treatment with hydrogen at elevated temperature prior to the commencement of the hydrogenation of nitrobenzene. The said elevated temperature is, for example, in the range of from 200° to 400° C., preferably in the range of from 200° to 380° C.

The said catalysts are eminently suitable for use in the hydrogenation of nitrobenzene to aniline.

If the activity of the catalyst employed should fall, it can easily be regenerated in situ, that is, in the hydrogenation reactor. For this purpose the catalyst is treated at between 350° and 400° C. in turn with steam, with a nitrogen/air mixture or atmospheric air, and finally nitrogen. The treatment with steam can be carried out for from 1 to 3 hours and the treatment with air or with the nitrogen/air mixture, for from 1 to 4 hours. A regeneration of this kind is not possible for precious metal catalysts other than on the carbon supports described, for example, with activated carbon as support, since an activated carbon begins to undergo combustion during a regeneration of this kind. For renewed activation of the catalyst, a treatment with hydrogen at between 200° and 400° C. can follow.

These catalysts are operated in the temperature range below 480° C., preferably below 460° C., most preferably below 440° C.

The contacts stated to be preferred render possible a particularly long operating time between regenerations.

In principle the catalyst grains can be in any form such as, for example, spheres, rods, Raschig rings, granules or pellets. Preferably shaped bodies are used which provide beds having a low flow resistance together with a good gas-surface contact, such as for example, Raschig rings, saddles, cartwheels and spirals.

The process according to the invention permits the vapour phase hydrogenation to be conducted particularly advantageously and this results in consistently high selectivities of aromatic amine and in long catalyst residence times between regenerations of the catalyst, which generally involve burning-off of carbonaceous deposits.

One procedure involves operating at constant pressure and starting with a particularly high loading (g/ml.h) of catalyst. The loading is then decreased in the course of deactivation of the catalyst during the operating time between two regenerations, so that no aromatic nitro compound breaks through.

Another equally effective method involves maintaining the loading (g/ml.h) of catalyst constant and beginning with a low pressure in the system; the pressure in the system is slowly increased before the aromatic nitro compound begins to break through.

A mode of operation between the two extremes of constant pressure and constant loading (g/ml.h) can also be selected. It is preferable to start with a low pressure and a low loading and then to increase both of these in the course of deactivation of the catalyst.

The loading of the catalysts can be very high in the process according to the invention, and may amount to from 0.1 g up to 20 g of aromatic nitro compound per ml of catalyst and per hour, preferably up to 15 g/ml.h, particularly preferably up to 10 g/ml.h, most preferably up to 5 g/ml.h.

The process according to the invention is distinguished therefore by high production outputs associated with a reduction in unit sizes. The process according to the invention also permits the use of single standard units and renders possible high plant capacities at low investment costs. The process is particularly suitable for the conversion of nitrobenzene to aniline.

FIG. 1 and FIG. 2 illustrate three reactors connected in series (FIG. 1) or three reactors connected in parallel (FIG. 2). The arrangement illustrated in FIG. 1 was used in Example 9. The arrangement illustrated in FIG. 2 was used in Example 10. The units shown in each of these Figures are: I=evaporator; II, III, IV=three reactors; V, VI, VII=three steam generators (in FIG. 2, only one); VIII=distillation column; IX=condenser; X=separating vessel having two constant-level devices. The streams of materials represented are:

1=$H_2$; 2=nitroaromatic compound (e.g., nitrobenzene); 3, 4, 5=feeds for $H_2$/nitrobenzene vapor mixture into the reactors II, III and IV; 6, 7, 8=hydrogenated reaction mixture from the reactors II, III and IV, which in FIG. 1, after being cooled for the production of useful steam, is led into the next reactor with the introduction of fresh $H_2$/nitrobenzene vapor mixture and in FIG. 2 is collected and together fed to the unit for steam production; 9=boiler feed water; 10=useful steam; 11=$H_2O$-containing aniline from the bottom of VIII; 12=$H_2O$/aniline vapor mixture; 13=return flow to VIII and feed to X; 14 $H_2O$-containing aniline from X; 15=collection collecting main for $H_2O$-containing aniline for further working up; 16=aniline-containing water from X for further working up; 17=waste gas, which due to its content of hydrogen is returned in large part to the process (not shown) while a minor part is disposed of (e.g., by combustion).

Having thus described our invention, the following Examples are given as being illustrative thereof. All parts and percentages given in these Examples are parts by weight or percentages by weight, unless otherwise indicated.

EXAMPLES

Example 1

4000 g of granular graphite EG 17 from the firm Ringsdorf, (granules of 1 to 3 mm, tap density 650 to 1000 g/l, BET=0.3 to 0.4 $m^2/g$) having an absorption capacity of 7 ml of acetonitrile per 100 g of support was placed in a rotatable vessel and to this was added a solution of 16.6 g of palladium(II) acetate in 260 g of acetonitrile. The mixture was agitated by rotation until the solution had been completely absorbed by the support material. The solid material was then dried for five minutes in a strong ascending stream of warm air at 40° C. The dried catalyst was subsequently reduced for a period of 3 hours in a hot stream of hydrogen at 100° C.

Example 2

5000 ml of α-$Al_2O_3$ from the firm Condea, (α-alumina, density 1.02 g/ml, spheres having a diameter of 1 mm, BET=4 $m^2/g$) having an absorption capacity of 33.4 ml of water per 100 g of support, was placed in a rotatable vessel and to this was added a solution of 553 g of disodium tetrachloro-palladate in 1200 g of water. The mixture was stirred by rotation until the entire solution had been absorbed by the support material. The solid material was then dried for ten minutes in a strong ascending stream of warm air at 40° C. The dried catalyst was reduced by means of hydrogen at 350° C. for a period of 3 hours, a solution of 500 g of oxalic acid dihydrate and 178.6 g of vanadium pentoxide in 1030 g of water was then added at room temperature to the reduced and dried solid material and the mixture was stirred by rotation until the entire solution had been absorbed by the support material. The solid material was then dried for ten minutes in a strong ascending stream of warm air at 40° C., followed by impregnation once again with the identical quantity of a vanadium oxalate solution and subsequent drying in the stream of warm air. The dried catalyst was tempered for 4 hours at 300° C. and then cooled to room temperature. There followed impregnation of the solid material, as described above, by a solution of 128.2 g of lead(II) acetate trihydrate in 1200 g of water. The solid material was then again dried for ten minutes in a strong ascending stream of warm air at 40° C., the dried catalyst was reduced by means of hydrogen at 350° C. for a period of 3 hours and finally washed at room temperature with distilled water until the washings showed a pH value of 7.

The catalyst thus obtained underwent a final drying for ten minutes in a strong ascending stream of warm air at 40° C.

Example 3

4000 g of needle coke from the firm Grafogran GmbH (granules of 1 to 4 mm, BET=1.0 to 1.1 m$^2$/g) having an absorption capacity of 35 ml of water per 100 g of support was placed in a rotatable vessel and to this was added a solution of 16.6 g of palladium(II) acetate in 260 g of acetonitrile. The mixture was stirred by rotation until the entire solution had been absorbed by the support material. The solid material was then dried for five minutes in a strong ascending stream of warm air at 40° C. The dried catalyst was then reduced for a period of 3 hours in a hot stream of hydrogen at 100° C.

Example 4

5000 ml of α-Al$_2$O$_3$ from the firm Condea, (α-alumina, density 1.02 g/ml, spheres having a diameter of 1 mm, BET=4 m$^2$/g) having an absorption capacity of 33.4 ml of water per 100 g of support, was placed in a rotatable vessel and to this was added a solution of 415 g of disodium tetrachloro-palladate in 1200 g of water. The mixture was stirred by rotation until the entire solution had been absorbed by the support material. The solid material was then dried for ten minutes in a strong ascending stream of warm air at 40° C. whereupon the process of impregnation and drying was repeated. The dried catalyst was reduced by means of hydrogen at 350° C. for a period of 3 hours. A solution of 500 g of oxalic acid dihydrate and 178.2 g of vanadium pentoxide in 1030 g of water was then added at room temperature to the reduced and dried solid material and the mixture was stirred by rotation until the entire solution had been absorbed by the support material. The solid material was then dried for ten minutes in a strong ascending stream of warm air at 40° C., whereupon two further impregnations with a vanadium oxalate solution and subsequent drying in the stream of warm air were carried out. The dried catalyst was tempered for 4 hours at 300° C. and then cooled to room temperature. There followed impregnation of the solid material by a solution of 192.4 g of lead(II) acetate trihydrate in 1200 g of water, as described in Example 2. The solid material was then again dried for ten minutes in a strong ascending stream of warm air at 40° C., the dried catalyst was reduced by means of hydrogen at 350° C. for a period of 3 hours and finally washed at room temperature with distilled water until the washings showed a pH value of 7. The catalyst thus obtained underwent a final drying for ten minutes in a strong ascending stream of warm air at 40° C.

Example 5

3000 ml (2860 g) of the catalyst produced in Example 1 was placed as a bed, 155 mm in height, in the middle of a pressure-resistant steel pipe (DIN 2463, $\phi_a$=168.3 mm, $\phi_i$=158.3 mm). Within the axis of the pipe a small steel tube was positioned, wherein a thermocouple could be moved axially. Beds of glass spheres were positioned above and underneath the catalyst bed. The pressure-resistant steel pipe was well insulated with fabric tape and arranged in a tubular furnace lined with fireclay and provided at the upper end with a pressure-resistant evaporator-superheater and at the lower end with a condenser having a collecting vessel and facility for continuous discharge of the product. A stream of hydrogen was sent at normal pressure through the evaporator-superheater, the reactor containing the catalyst and the condenser having continuous discharge of the product, and the catalyst was activated at 100° C. for 3 hours. Following this, the pressure in the plant was set at 2 bar and nitrobenzene was sent to the evaporator-superheater by means of a proportioning pump.

The experiment proceeded under the following general conditions: for each mol of nitrobenzene introduced, 81 moles of hydrogen were led into the evaporator-superheater; the heating of the superheater and of the tubular furnace was controlled so that at no position did the temperature of the catalyst exceed 400° C. and the loading of the catalyst was 1 g of nitrobenzene per ml of bed and per hour. The analysis of the condensate by gas chromatography after 24 hours showed that 99.9% of the nitrobenzene was converted and that aniline having a selectivity of more than 99.8% was formed.

During the next 500 hours, the pressure and loading were increased in steps to 4 bar and 3 g/ml.h, with the temperature of the catalyst being permitted to rise to 440° C. at above 3 bar. The analysis of the condensate by gas chromatography showed 100% conversion with a selectivity as regards aniline of better than 99.5%. With a loading of 3 g/ml.h, a ratio of nitrobenzene to water of 1 to 81, at a maximum temperature of the catalyst of 440° C. and a total pressure of 4 bar, the experiment was continued for a further 500 hours without any sign of incipient deactivation of the catalyst, and was then terminated.

Example 6

2800 ml (3560 g) of the catalyst produced in Example 2 was placed as a bed, 160 mm in height, in the installation described in Example 5. The catalyst then underwent conditioning for 48 hours at 480° C. and 5 bar in the stream of hydrogen. The pressure was then lowered to normal pressure and nitrobenzene and hydrogen in a molar ratio of 1 to 81 were fed into the evaporator-superheater. The loading was adjusted to 1.5 g/ml.h in respect of nitrobenzene and the temperature of the superheater and of the tubular furnace were selected so that at no position was the catalyst hotter than 445° C. After 12 hours the pressure was reduced to 2 bar. After a further 12 hours the loading was increased to 3 g/ml.h and the total pressure to 4 bar. Analyses by gas chromatography of the condensate collected consistently showed up to this point in time an 100% conversion with selectivities as regards aniline of better than 95%.

After 100 hours the total pressure was increased to 8 bar.

After 200 hours the total pressure was increased to 12 bar. After 400 hours the total pressure was increased to 16 bar and the loading was raised to 5 g/ml.h. After 600 hours the total pressure was increased to 20 bar. After 800 hours the experiment was terminated at 100% conversion and a selectivity as regards aniline of 99.7%, without there being any sign of deactivation of the catalyst. During the experiment, the position at which the catalyst attained a temperature of 445° C. moved from the beginning of the catalyst bed 100 mm towards the end of the catalyst bed.

Example 7

220 ml (145.7 g) of the catalyst produced in Example 3 was placed, with a bed height of 180 mm, in a very well-insulated tubular glass reactor. The reactor was provided at six points with devices for measuring temperature. The first measuring point $T_E$ was positioned directly above the catalyst bed, $T_{K1}$ to $T_{K4}$ were in the catalyst bed, each at a distance apart of 4 cm, beginning at a bed height of 2 cm, and the sixth measuring point $T_A$ was positioned directly under the catalyst bed. The tubular glass reactor was equipped at the upper end with an evaporator-superheater. For the continuous removal of the product gas, a well-insulated glass tube was connected to the outlet of the reactor. This glass tube led the product away for condensation in a system of multitubular condensers and coiled-tube condensers. The catalyst was first of all activated for 10 hours at 200° C. in the reactor at normal pressure, with the introduction of hydrogen via evaporators and superheaters. The stream of hydrogen was then adjusted to 1620 l/h. At initial temperatures of $T_E$=201° C., $T_{K1}$=198° C., $T_{K2}$=198° C., $T_{K3}$=198° C., $T_{K4}$=197° C., $T_A$=197° C., 110 g/h of nitrobenzene was fed by means of a proportioning pump via the evaporator-superheater into the stream of hydrogen; this corresponded to a 2600 molar excess of hydrogen, referred to nitrobenzene. After several hours the following temperatures were established: $T_E$=207° C., $T_{K1}$=329° C., $T_{K2}$=370° C., $T_{K3}$=376° C., $T_{K4}$=366° C., $T_A$=365° C. The analysis of the condensate by gas chromatography after 40 hours showed a conversion of 99,98% and a selectivity of 99.5%. After 170 hours, the selectivity for aniline rose to more than 99.6%. After 1700 hours the experiment was terminated without any sign of incipient deactivation of the catalyst.

Example 8

Similarly to Example 7, 220 ml (298.9 g) of catalyst from Example 4 was placed in the same reactor as was used in Example 7. Following a reduction similar to that in Example 7, at initial temperatures of $T_E$=208° C., $T_{K1}$=212° C., $T_{K2}$=210° C., $T_{K3}$=208° C., $T_{K4}$=206° C., $T_A$=203° C., on the measured addition of nitrobenzene under otherwise identical conditions, the following temperatures were attained:

$T_E$=218° C., $T_{K1}$=300° C., $T_{K2}$=385° C., $T_{K3}$=380° C., $T_{K4}$=375° C., $T_A$=376° C. After 8 hours, with a quantitative conversion, an aniline selectivity of 98.5% was attained. A further analysis by gas chromatography after 251 hours showed a selectivity for aniline of more than 99.95%. After 1100 hours, small quantities of nitrobenzene indicated incipient deactivation of the catalyst.

Example 9

The process was carried out in an industrial plant, as represented in FIG. 1 and explained above in more detail. The following quantitative data (parts by weight per hour= T.) and temperatures relate to the flows of materials in FIG. 1:

Stream 1 was made up of 420.5 parts by weight per hour of $H_2$ plus 7.0 parts by weight per hour of $N_2$ at 20° C.

Stream 2 was made up of 8108.2 parts by weight of nitrobenzene per hour at 20° C.

Stream 3 was made up of 2383 parts by weight per hour of nitrobenzene plus 3441 parts by weight per hour of $H_2$ plus 181.5 parts by weight per hour of aniline plus 1237.3 parts by weight of $H_2O$ per hour plus 943.3 parts by weight of $N_2$ (including recycled waste gas) per hour at 220° C.

Stream 4 was made up of 2690 parts by weight per hour of nitrobenzene plus 3560.4 parts by weight of $H_2$ per hour plus 1989.4 parts by weight per hour of aniline plus 1971 parts by weight of $H_2O$ per hour plus 973 parts by weight of $N_2$(including waste gas portion) per hour at 220° C.

Stream 5 was made up of 3036 parts by weight of nitrobenzene per hour plus 3695 parts by weight of $H_2$ per hour plus 4030 parts by weight of aniline per hour plus 2799 parts by weight of $H_2O$ per hour plus 1006 parts by weight of $N_2$ (including waste gas portion) per hour at 220° C.

Stream 6 was made up of 3324 parts by weight of $H_2$ per hour plus 1984 parts by weight of aniline per hour plus 1934 parts by weight of $H_2O$ per hour plus 943.3 parts by weight of $N_2$ per hour at 400° C.

Stream 7 was made up of 3428.3 parts by weight of $H_2$ per hour plus 4024 parts by weight of aniline per hour plus 2758 parts of $H_2O$ per hour plus 973 parts by weight of $N_2$ per hour at 400° C.

Stream 8 was made up of 3546 parts by weight of $H_2$ per hour plus 6326 parts by weight of aniline per hour plus 3687 parts by weight of $H_2O$ per hour plus 1006 parts by weight of $N_2$ per hour at 400° C.

Stream 15 was made up of 6019 parts by weight of aniline per hour plus 97 parts by weight of $H_2O$ per hour at 110° C.

Stream 16 was made up of 113.4 parts by weight of aniline per hour plus 2267.5 parts by weight of $H_2O$ per hour at 60° C.

Stream 17 was made up of 3546 parts by weight of $H_2$ per hour (of which 3523.8 parts by weight per hour were returned to the process and 22.2 parts by weight per hour were removed for disposal) plus 194 parts by weight of aniline per hour (192.8 parts by weight per hour were returned to the process; 1.2 parts by weight per hour were removed) plus 1323 parts by weight of $H_2O$ per hour (1314.7 parts by weight per hour were returned to the process; 8.3 parts by weight per hour were removed) plus 1006 parts by weight per hour of $N_2$ (999 parts by weight per hour were returned to the process; 7 parts by weight per hour were removed) at 600° C.

The pressure was maintained in the range of from 5 to 5.5 bar during this procedure. The reaction mixture was cooled down to 180° C. after exiting the final steam generator.

Example 10

Nitrobenzene was hydrogenated in accordance with the process of the present invention in equipment arranged as illustrated in FIG. 2. The following quantitative data and temperatures relate to the flow of materials in FIG. 2:

Stream 1 was made up of 747.4 parts by weight of $H_2$ per hour plus 7 parts by weight per hour of $N_2$ at 200° C.

Stream 2 was made up of 8108.3 parts by weight of nitrobenzene per hour at 200° C.

Streams 3, 4, and 5 were equal and combined were made up of 8108.3 parts by weight per hour of nitrobenzene plus 11208.5 parts by weight of $H_2$ per hour plus 589 parts by weight per hour of aniline plus 3942.4 parts by weight per hour of $H_2O$ plus 1007 parts by weight of $N_2$ (with waste gas portion) at 210° C. Streams 6, 7 and 8 were equal and combined were made up of 10810.5 parts by weight of $H_2$ per hour plus 6722.6 parts by weight of aniline per hour plus 6315.4 parts by weight of $H_2O$ per hour plus 1007 parts by weight of $N_2$ per hour at 400° C.

Stream 15 was made up of 6022 parts by weight of aniline per hour plus 200.6 parts by weight of $H_2O$ per hour at 84° C.

Stream 16 was made up of 107 parts by weight of aniline per hour plus 2144 parts by weight of $H_2O$ per hour at 60° C.

Stream 17 was made up of 10810.5 parts by weight of $H_2$ per hour (10734 parts by weight per hour were returned, 76.6 parts by weight per hour were removed) plus 593.2 parts by weight of aniline per hour (589 parts by weight per hour were returned; 4.2 parts by weight per hour removed) plus 3970.5 parts by weight of $H_2O$ per hour (3942.5 parts by weight per hour were returned; 28 parts by weight per hour were removed) plus 1007 parts by weight per hour of $N_2$ (1000 parts by weight per hour were returned; 7 parts by weight per hour were removed) at 60° C.

The pressure was maintained in the range of from about 5 to about 5.5 bar throughout the process. The reaction mixture was cooled down to 140° C. after leaving the final steam generator.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an aromatic amine represented by the formula

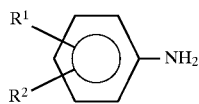

(I)

in which
R¹ represents hydrogen, a methyl group, an ethyl group or an amino group, and
R² represents hydrogen, a methyl group or an ethyl group
comprising hydrogenating an aromatic nitro compound represented by the formula

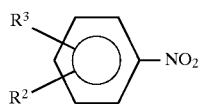

in which
R² represents hydrogen, a methyl group or an ethyl group, and
R³ represents hydrogen, a methyl group, an ethyl group or a nitro group
with hydrogen on a fixed catalyst under adiabatic conditions at a pressure of from 1 to 30 bar in which the nitro compound and hydrogen are introduced into a reaction vessel at a temperature of from about 200° to about 400° C. and the maximum catalyst temperature is 500° C.

2. The process of claim 1 in which the hydrogenation reaction is carried out at from 1 to 20 bar pressure.

3. The process of claim 1 in which the hydrogenation reaction is carried out at from 1 to 15 bar pressure.

4. The process of claim 1 in which the nitro compound and hydrogen are introduced at a temperature of from about 230° to about 370° C.

5. The process of claim 1 in which the nitro compound and hydrogen are introduced at a temperature of from about 250° to about 350° C.

6. The process of claim 1 in which R² represents hydrogen.

7. The process of claim 1 in which R² represents hydrogen and R³ represents hydrogen.

8. The process of claim 1 in which the reaction is carried out in from 2 to 10 reactors connected in series.

9. The process of claim 1 in which the reaction is carried out in from 2 to 5 reactors connected in series.

10. The process of claim 1 in which the reaction is carried out in 2 or 3 reactors connected in series.

11. The process of claim 1 in which the reaction is carried out in from 2 to 5 reactors connected in parallel.

12. The process of claim 1 in which the reaction is carried out in 2 or 3 reactors connected in parallel.

13. The process in claim 1 in which accumulated heat of reaction is used to generate a vapor.

14. The process of claim 8 in which nitroaromatic compound is fed to each reactor.

15. The process of claim 1 in which the fixed catalyst has a penetrable depth of from about 1 cm to about 5 m.

16. The process of claim 1 in which the fixed catalyst has a penetrable depth of from about 5 cm to about 2 m.

17. The process of claim 1 in which the fixed catalyst has a penetrable depth of from about 10 cm to about 1 m.

18. The process of claim 1 in which the fixed catalyst has a penetrable depth of from about 30 cm to about 60 cm.

19. The process of claim 1 in which the fixed catalyst is palladium on an α-alumina support.

20. The process of claim 1 in which the fixed catalyst is made up of
(a) from about 1 to about 100 g of at least one metal selected from Groups VIIIa, Ib and IIb of the Periodic Table of Elements (Mendeleev),
(b) from about 1 to about 100 g of at least one transition metal selected from Groups IIb, IVa, Va and VIa of the Periodic Table of Elements (Mendeleev), and
(c) from about 1 to about 100 g of at least one element selected from Groups IVb and Vb of the Periodic Table of Elements (Mendeleev)
per liter of inert support and has a BET surface area of less than 20 m²/g.

21. The process of claim 20 in which (a), (b) and (c) are arranged in the form of a shell on a support.

22. The process of claim 20 in which from about 20 to about 60 g of (a), from about 20 to about 60 g of (b) and from about 10 to about 40 g of (c) are present.

23. The process of claim 1 in which the fixed catalyst is made up of
(a) from about 20 to about 60 g of Pd per liter of catalyst,
(b) from about 20 to about 60 g of at least one transition metal selected from Ti, V, Nb, Ta, Cr, Mo and W per liter of catalyst, and
(c) from about 10 to about 40 g of Pb and/or Bi per liter of catalyst
on an α-alumina support having a BET surface area of less than 20 m²/g.

24. The process of claim 23 in which the fixed catalyst has a BET surface area of less than 10 m²/g.

25. The process of claim 1 in which the fixed catalyst is a palladium catalyst on a carbon support having a BET surface area of from about 0.2 to about 10 m²/g.

26. The process of claim 25 in which the palladium is present in an amount of from 0.001 to about 1.5% by weight based on total weight of catalyst.

27. The process of claim 26 in which up to 40% by weight of the palladium is replaced by one or more metals selected from Rh, Ir and Ru.

28. The process of claim 27 in which the catalyst further includes from 0.1 to 2% by weight (based on sulfur and/or phosphorus) of a sulfur-containing compound and/or phosphorus-containing compound.

29. The process of claim 27 in which the catalyst further includes from 0.1 to 1% by weight of a sulfur-containing compound and/or phosphorus-containing compound.

30. The process of claim 28 in which the catalyst includes a phosphorus-containing compound.

31. A process for the production of aniline comprising hydrogenating nitrobenzene with hydrogen on a fixed palladium catalyst on a carbon support under adiabatic conditions at a pressure of from about 5 to about 5.5 bar in which the nitrobenzene and hydrogen are introduced into a reaction vessel at a temperature of from about 200° to about 220° C. and the maximum catalyst temperature is 500° C.

* * * * *